United States Patent
Clark

(10) Patent No.: US 7,087,060 B2
(45) Date of Patent: Aug. 8, 2006

(54) METHODS FOR OBTAINING HEMOSTASIS OF PERCUTANEOUS WOUNDS

(75) Inventor: Timothy W. Clark, Philadelphia, PA (US)

(73) Assignee: Trustees of the University of Pennsylvania, Philadelphia, PA (US)

(*) Notice: Subject to any disclaimer, the term of this patent is extended or adjusted under 35 U.S.C. 154(b) by 141 days.

(21) Appl. No.: 10/198,161

(22) Filed: Jul. 19, 2002

(65) Prior Publication Data

US 2003/0028203 A1 Feb. 6, 2003

Related U.S. Application Data

(60) Provisional application No. 60/307,042, filed on Jul. 20, 2001.

(51) Int. Cl.
*A61B 17/04* (2006.01)

(52) U.S. Cl. .................. 606/111; 606/112; 606/113; 606/232

(58) Field of Classification Search ............ 606/232, 606/111–113
See application file for complete search history.

(56) References Cited

U.S. PATENT DOCUMENTS

| | | | |
|---|---|---|---|
| 4,796,626 A | 1/1989 | DeVries | 128/334 R |
| 5,741,301 A | 4/1998 | Pagedas | 606/232 |
| 6,015,428 A | 1/2000 | Pagedas | 606/232 |

OTHER PUBLICATIONS

Vorwerk, Konner, Schurmann, and Gunther, a Simple Trick to Facilitate Bleeding Control after Percutaneous Hemodialysis Fistula and Graft Interventions, Cardiovasc Intervent Radiol 20 (2) : 159-60 (1997).
Zaleski, Funaki, Gentile, and Garofalo, Purse-string Sutures and Miniature Tourniquet to Achieve Immediate Hemostasis of Percutaneous Grafts and Fistulas: a Simple Trick with a Twist, Am. J. Roentgenol. 175 (6) : 1643-5 (2000)
Simmons, Clark, and Rajan, The Woggle Technique: A New Method of Suture Closure of Hemodialysis Arteriovenous Grafts and Fistulae After Percutaneous Intervention, Journal of Vascular and Interventional Radiology 12(1) :S30 (2001).

*Primary Examiner*—Gary Jackson
(74) *Attorney, Agent, or Firm*—Gary M. Nath; Viviana Amzel; Lee C. Heiman

(57) ABSTRACT

This invention relates to novel methods, kits, and devices for stopping hemorrhaging of percutaneous wounds. The inventive subject matter involves insertion of a purse-string suture around the wound, insertion of the free two ends of the suture through a tension collar, manual tightening of the tension collar until hemostasis is achieved, and application of a suture lock to the free ends of the suture to secure the tension collar and maintain hemostasis. After a sufficient period of time to allow complete hemostasis, the suture lock and the tension collar are loosened; if hemostasis has been achieved, the suture lock, the tension collar, and the suture material are removed. If bleeding continues from the wound, the tension collar is tightened and the suture lock reapplied. This process may be repeated until complete hemostasis is achieved, without the need for additional suturing or manual compression.

3 Claims, 2 Drawing Sheets

METHODS FOR OBTAINING HEMOSTASIS OF PERCUTANEOUS WOUNDS

This application claims the benefit of U.S. Provisional Patent Application No. 60/307,042, filed on Jul. 20, 2001, the entire contents of which are herein incorporated by reference.

BACKGROUND OF THE INVENTION

1. Field of Invention

The present invention relates to novel methods for stopping hemorrhaging of percutaneous wounds. The method comprises placement of a purse-string monofilament suture around the wound, insertion of the free two ends of the suture through a tension collar, manual tightening of the tension collar until hemostasis is achieved, and application of a suture lock to the free ends of the suture to secure the tension collar and maintain hemostasis. After a sufficient period of time for complete hemostasis, the suture lock and the tension collar are loosened; if hemostasis has been achieved, the suture lock, the tension collar, and the suture material are removed. If bleeding continues from the wound, the tension collar is tightened and the suture lock reapplied. This process may be repeated until complete hemostasis is achieved, without the need for additional suturing or manual compression. The present invention further relates to novel kits and devices for producing hemostasis of a percutaneous wound in an animal.

2. Background

Manual compression is used to obtain hemostasis of percutaneous wounds, including the puncture site following removal of vascular sheaths, catheters, and other devices used for percutaneous interventions. An effective device for obtaining puncture site hemostasis without manual compression would represent a substantial saving in physician time and improved efficiency in patient care. Such factors are of considerable importance to patients who must undergo repeated interventions, such as those receiving dialysis shunts (grafts and fistulae), and most especially those required to simultaneously take anticoagulants. Prolonged manual compression of 30–60 minutes is often required when anticoagulants such as heparin or large sheaths are used. Moreover, manual compression itself may compromise blood flow through the dialysis shunt, leading to clot formation. Similar considerations of time and efficiency apply to the need for wound closure of, for example, wounds caused by puncture, gunshot, or other roughly circular injury.

Various techniques of suture closure have been described to facilitate hemostasis at the puncture site. Many physicians have used the purse-string technique to achieve hemostasis. Although effective, the suture can be very difficult to remove because the knot tends to get buried within the tissues around the puncture sites, which can become quite puckered. The suture knot is then just a few millimeters away from the high flow hemodialysis vascular access and hemodialysis nurses are often reluctant to remove the sutures at the next dialysis session. Patients returning weeks to months after purse-string suture insertion for follow-up interventions would still have the previous sutures left in place. Thus, there is an acute need for a method that makes suture removal simple and safe, and wherein the patient does not have any suture material remaining.

Previously reported techniques for obtaining hemostasis following percutaneous intervention or injury include purse-string sutures with a temporary knot, a tourniquet device, or a hemostat to tighten the purse-string suture (see Vorwerk, Konner, Schurmann, and Gunther, a *Simple Trick to Facilitate Bleeding Control after Percutaneous Hemodialysis Fistula and Graft Interventions,* Cardiovasc Intervent Radiol 20(2):159–60 (1997); Zaleski, Funaki, Gentile, and Garofalo, *Purse-string Sutures and Miniature Tourniquet to Achieve Immediate Hemostasis of Percutaneous Grafts and Fistulas: a Simple Trick with a Twist,* Am. J. Roentgenol. 175(6):1643–5 (2000); and Simons, Clark, and Rajan, *The Woggle Technique: A New Method of Suture Closure of Hemodialysis Arteriovenous Grafts and Fistulae After Percutaneous Intervention,* Journal of Vascular and Interventional Radiology 12(1):S30 (2001)). A temporary knot fails to allow a means of providing rapid and reversible tension on the puncture site. A tourniquet device passes through a loop of purse-string suture and achieves hemostasis through twisting and traction of the skin at the puncture site.

U.S. Pat. No. 6,355,050, issued to Andreas, et al., on Mar. 12, 2002 discloses a device and method for suturing a tissue layer having two sides by releasably retaining at least a portion of the suture in a stationary position on one side of the tissue layer, wherein the portion of the suture is retrieved through the tissue layer from the opposite side whereby the suture is drawn from one side to the opposite side; in particular, Andreas, et al., disclose devices and methods for suturing the wall of a tubular graft and a graft anastomosis assembly.

U.S. Pat. No. 6,117,145, issued to Wood, et al., on Sep. 12, 2000, discloses a method and device for providing hemostasis at vascular penetration sites utilizing a blood vessel puncture occlusion device.

U.S. Pat. No. 6,036,699, issued to Andreas, et al. on Mar. 14, 2000, discloses medical devices and methods for suturing tissue by proximally drawing sutures through a tissue layer in the proximity of an aperture; suturing vascular tissue while maintaining adequate perfusion or hemostasis, or both; anastomosing a graft to an aperture in a vessel wall while maintaining hemostasis at the anastomosis with physiological flow and/or pressure in the vessel lumen; punching and removing tissue to form an aperture in a vessel wall while maintaining hemostasis at the aperture with physiological flow and/or pressure in the vessel lumen; automatically and repeatably placing suture thread through vessel wall tissue surrounding an aperture in the vessel wall in a suture pattern that is useful for anastomosing a tubular graft to the aperture; and, deploying a suture with one end extending through the tissue that surrounds a punched aperture in a vessel wall and the opposite suture end extending radially through a tubular graft wall adjacent an open end of the graft, such that a vessel anastomosis may be rapidly and repeatably performed in a CABG procedure even while the vessel is under physiological flow.

U.S. Pat. Nos. 6,015,428, 5,741,301, and 5,895,393, issued to Pagedas, respectively disclose an integrally formed suture and suture lock, a self locking suture lock, and a suture lock holder.

Statistically, the need for improved hemostasis devices is demonstrated by the number of prevalent patients in the United States with end-stage renal disease, which is expected to increase from 326,000 in 1998 to over 666,000 by 2010. Most of these patients will receive renal replacement therapy through hemodialysis. For a large portion of these patients, percutaneous access will be necessary to maintain dialysis shunt function. These patients also require ongoing periodic radiologic treatments with angioplasty balloons, stents, and clot removal devices to maintain dialysis shunt function. According to the United States Renal Data System, Medicare expenditures on dialysis access totaled nearly 1 billion dollars in 1994. Since that time, progressive escalation in the number of dialysis interventions has occurred. From 1991 to 1998, a 65% increase in prevalent dialysis patients was observed with a 100% increase in shunt blood clot removal procedures (declots) and a 65% increase in angioplasty and other procedures (revisions).

The duration of bleeding is highly variable among patients and depends on many factors, including the size of the vascular sheath used for the treatment procedure, the dose and elimination of heparin and other blood thinning agents, the anatomy of the patient, and the hemodynamic pressure within the dialysis shunt. Because patients will differ in bleeding tendency, a simple and effective means of reapplying tension to the puncture site is highly advantageous.

The prior art tourniquet devices pass through a single loop of purse-string suture and achieve hemostasis through twisting and traction of the skin at the puncture site. This produces unnecessary distortion of the puncture site, which, in Applicant's experience, leads to rebleeding once the tourniquet has been loosened. The present inventive methods and devices provide uniform, circumferential tension around the puncture site and can be quickly reapplied when necessary, while producing minimal distortion or traction on the skin.

Further, by removing the suture the same day as the surgery, there is a decreased risk of infection when compared to leaving in a suture for several days. When using the methods of the present invention, the requirements for coagulation testing prior to intervention may be relaxed. In patients with elevated INR, we have successfully performed interventions without complication, although we leave the hemostasis device on longer.

Thus, the present invention provides a simple, rapid method for obtaining a puncture site hemostasis following percutaneous intervention or injury, particularly of dialysis shunts and the like. The inventive methods provide uniform, circumferential tension around the puncture site and can be quickly reapplied when necessary. The potential benefits and advantages over existing techniques include rapid and reversible tension on the puncture site, reduced twisting and traction of the skin at the puncture site, and reduced physician intervention and improved efficiency in patient care resulting lower cost of medical care. Further, the inventive methods consistently obviate the need for follow-up appointments to remove a purse-string suture at a later date.

SUMMARY OF THE INVENTION

The present invention relates to a method for producing hemostasis of a percutaneous wound in an animal, which comprises the steps of:
(i) inserting a purse-string suture around the percutaneous wound using multiple passes of a suture needle and a physiologically suitable suture material, wherein a final pass of the suture needle is oriented to bring the final exit site of the suture material substantially adjacent to an initial entry site of the suture material through the skin of said animal;
(ii) bringing the initial entry and final exit limbs of the suture material through a tension collar;
(iii) tightening the tension collar until hemostasis of said percutaneous wound in an animal is achieved; and
(iv) applying a suitable suture lock to the free ends of the suture material to secure the tension collar.

The present invention further relates to a method for producing hemostasis of a percutaneous wound produced by the insertion of a vascular sheath, cannula, or catheter in the skin of an animal, which comprises the steps of:
(i) inserting a purse-string suture within 3 mm of the percutaneous wound, using a suture needle and a physiologically suitable suture material, wherein said purse-string suture is produced through three or four needle passes of monofilament 2.0 polypropylene or nylon, and wherein a final pass of the suture needle is oriented to bring the final exit site of the suture material substantially adjacent to an initial entry site of the suture material through the skin;
(ii) bringing the initial entry and final exit limbs of the suture material through a tension collar while said vascular sheath, cannula, or catheter is inserted through the skin;
(iii) manually tightening the tension collar, after removal of said vascular sheath, cannula, or catheter, until hemostasis is achieved;
(iv) applying a suitable suture lock to the free ends of the suture material to secure the tension collar;
(v) releasing said suture lock and loosening said tension collar after a sufficient period of time for hemostasis;
(vi) optionally retightening said tension collar and reapplying said suture lock if required to prevent continued bleeding or oozing of blood; and
(vii) removing said tension collar, suture lock, and suture material when satisfactory hemostasis has been achieved.

The present invention also relates to a kit for producing hemostasis of a percutaneous wound in an animal, comprising:
(a) a suture of acceptable size and material characteristics suitable for the type and location of the percutaneous wound to be treated;
(b) a suture needle;
(c) a tension collar; and
(d) a suture-lock.

Finally, the present invention relates to a body comprising two hollow shaft portions (1) and (2), each having one or more exterior wall(s) and an internal channel (3), and a cavity portion (4) located between said shaft portions; and
(ii) a slide-spring lock mechanism within said cavity portion for providing a suture-locking effect within the hemostasis device, said slide-spring lock mechanism having a plunger (5) mounted slidably in said passage for movement relative to said cavity portion along a predetermined axis, and having an end portion (6) which is accessible from the outside of the cavity portion for manually pressing the plunger inwardly along said axis from a gripping position to a released position, said cavity portion having one or more aperture(s) (7) and said plunger having one or more aperture(s) (8) through which one or more suture(s) (9) can extend generally transversely of said axis, wherein said slide-spring lock mechanism is in sliding engagement with one or more length(s) of suture material, said slide-spring lock mechanism being capable of releasable locking engagement along said length(s) of suture material.

DETAILED DESCRIPTION OF THE INVENTION

Definitions

Figure 1:
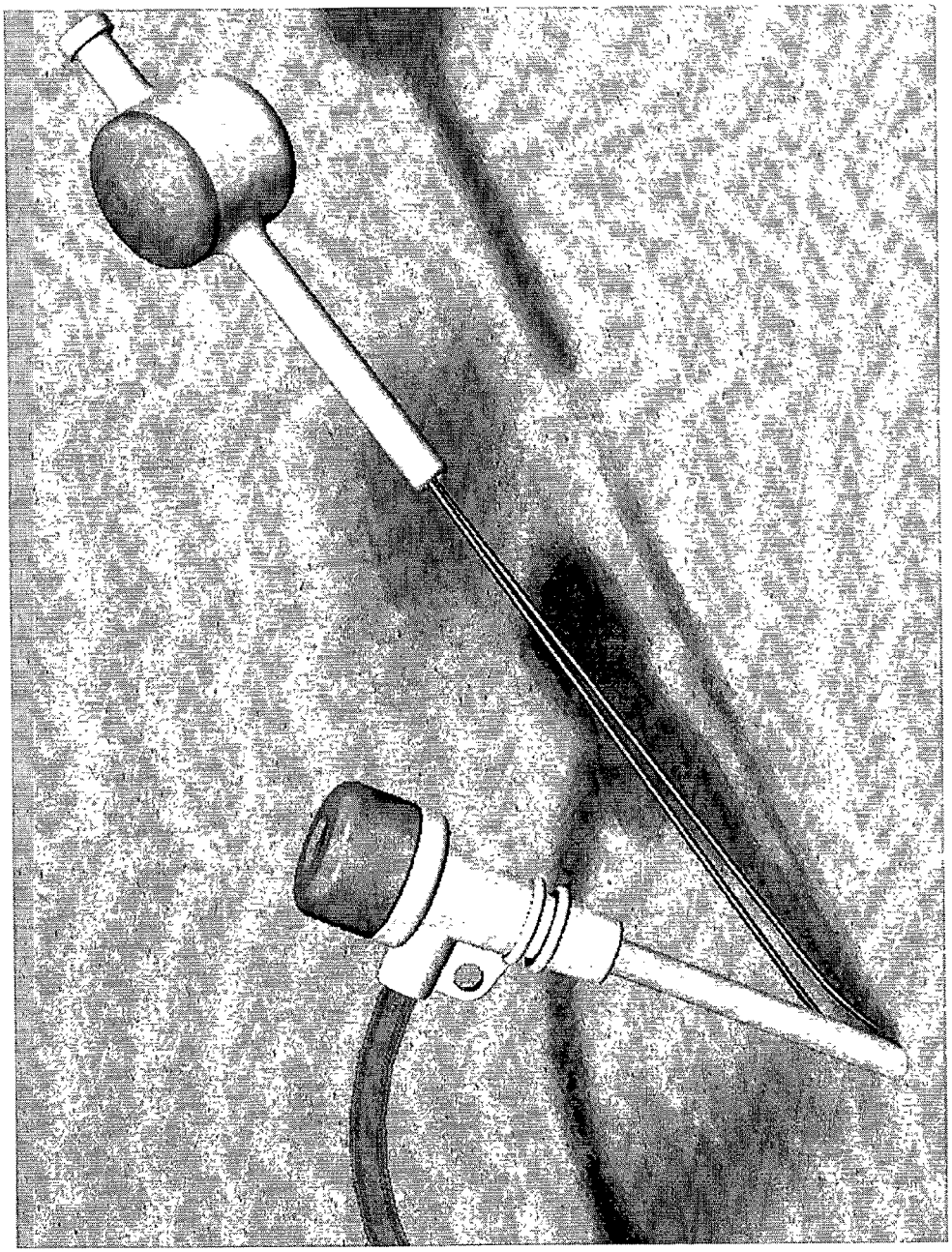
FIG. 1 is a CAD drawing which depicts a purse-string suture placed around a percutaneous sheath, with the final pass of the suture needle oriented to bring the exit site of the suture material adjacent to the initial entry site of the suture material through the skin, and two limbs of the suture material brought through the tension collar of a releasable hemostasis device of the present invention.
Figure 2:
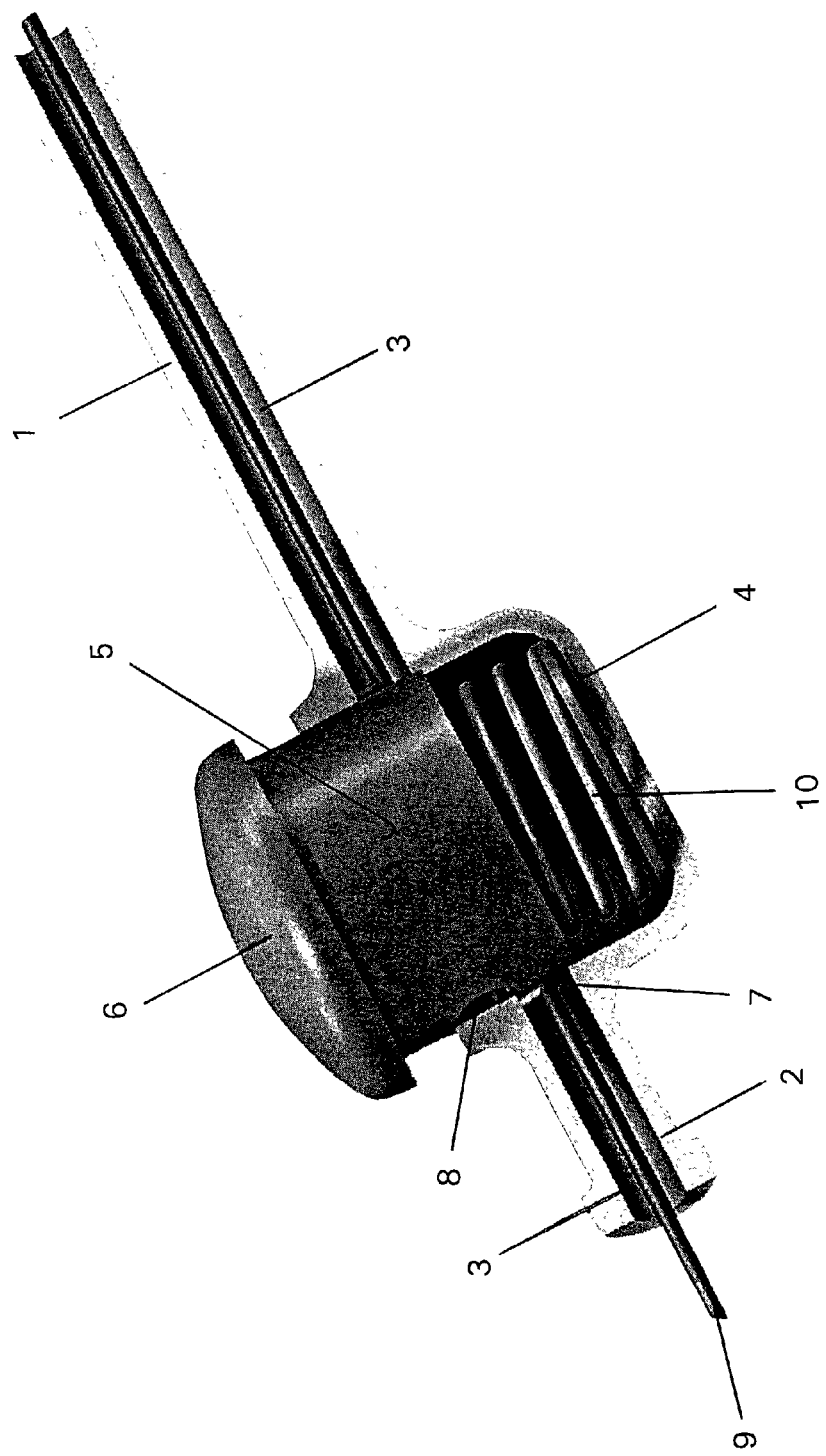
FIG. 2 is a CAD drawing which depicts a cutaway view of a releasable hemostasis device of the present invention, with the slide-spring lock mechanism biased in the locked "closed", or gripping, orientation.

"Adjacent" refers to things which are near in space or position; immediately adjoining without significant intervening space.

Methods of the Present Invention

The present invention relates to a method for producing hemostasis of a percutaneous wound in an animal, which comprises the steps of:
 (i) inserting a purse-string suture around the percutaneous wound using multiple passes of a suture needle and a physiologically suitable suture material, wherein a final pass of the suture needle is oriented to bring the final exit site of the suture material substantially adjacent to an initial entry site of the suture material through the skin of said animal;
 (ii) bringing the initial entry and final exit limbs of the suture material through a tension collar;
 (iii) tightening the tension collar until hemostasis of said percutaneous wound in an animal is achieved; and
 (iv) applying a suitable suture lock to the free ends of the suture material to secure the tension collar.

In a preferred embodiment, the hemostasis device of the present invention consists of a tension collar, such as a plastic guide wire introducer, or a similar hollow, tube-shaped member placed over the ends of a purse string suture and secured with a suture locking device, such as a hemostat, a clamp, or a commercially-available suture lock to tighten the suture without making a knot. The device is applied immediately prior to removing the sheath or catheter at the end of a procedure. The suture and hemostasis device are left for 20–60 minutes, and then the hemostasis device is released by means of loosening the suture lock. If hemostasis is achieved, the suture is removed, and if hemostasis is not achieved the hemostasis device is either retightened or the suture is knotted and the patient discharged.

In another preferred embodiment, said percutaneous wound results from the insertion of a vascular sheath, cannula, or catheter through the skin of said animal. However, the methods and devices of the present invention are expected to be well suited to obtaining hemostasis of other wounds such as those resulting from gunshot, puncture with sharp implements such as knives, picks, and screwdrivers, and other injuries producing wounds which are substantially circular.

In another preferred embodiment, said purse-string suture is inserted while said vascular sheath, cannula, or catheter is also inserted through the skin. Inserting the suture while the surgical instrument is still in place is expected to further reduce the possibility of bleeding or infection.

In another preferred embodiment, said vascular sheath, cannula, or catheter is removed prior to tightening said tension collar.

In a further preferred embodiment, said suture material is monofilament 2.0 polypropylene or nylon.

In a further preferred embodiment, said purse-string suture is inserted within 3 mm of the percutaneous wound.

In a most preferred embodiment, said method comprises the additional steps of:
 (v) releasing said suture lock and loosening said tension collar after a sufficient period of time for hemostasis;
 (vi) retightening said tension collar and reapplying said suture lock, as required to prevent continued bleeding or oozing of blood; and
 (vii) removing said suture material when satisfactory hemostasis has been achieved.

In another preferred embodiment, the present invention relates to a method for producing hemostasis of a percutaneous wound produced by the insertion of a vascular sheath, cannula, or catheter in the skin of an animal, which comprises the steps of:
 (i) inserting a purse-string suture within 3 mm of the percutaneous wound, using a suture needle and a physiologically suitable suture material, wherein said purse-string suture is produced through three or four needle passes of monofilament 2.0 polypropylene or nylon, and wherein a final pass of the suture needle is oriented to bring the final exit site of the suture material substantially adjacent to an initial entry site of the suture material through the skin;
 (ii) bringing the initial entry and final exit limbs of the suture material through a tension collar while said vascular sheath, cannula, or catheter is inserted through the skin;
 (iii) manually tightening the tension collar, after removal of said vascular sheath, cannula, or catheter, until hemostasis is achieved;
 (iv) applying a suitable suture lock to the free ends of the suture material to secure the tension collar;
 (v) releasing said suture lock and loosening said tension collar after a sufficient period of time for hemostasis;
 (vi) optionally retightening said tension collar and reapplying said suture lock if required to prevent continued bleeding or oozing of blood; and
 (vii) removing said tension collar, suture lock, and suture material when satisfactory hemostasis has been achieved.

The present invention also relates to a kit for producing hemostasis of a percutaneous wound in an animal, comprising:
 (a) a suture of acceptable size and material characteristics suitable for the type and location of the percutaneous wound to be treated;
 (b) a suture needle;
 (c) a tension collar; and
 (d) a suture-lock.

In a preferred embodiment, said tension collar and suture-lock are optionally an integrated single unit.

In a preferred embodiment, said suture material is a nonabsorbable monofilament.

In a most preferred embodiment, said suture material is 2.0 monofilament polypropylene or nylon.

Finally, the present invention relates to a releasable hemostasis device comprising:
 (i) a body comprising two hollow shaft portions (1) and (2), each having one or more exterior wall(s) and an internal channel (3), and a cavity portion (4) located between said shaft portions; and
 (ii) a slide-spring lock mechanism within said cavity portion for providing a suture-locking effect within the hemostasis device, said slide-spring lock mechanism having a plunger (5) mounted slidably in said passage for movement relative to said cavity portion along a predetermined axis, and having an end portion (6) which is accessible from the outside of the cavity portion for manually pressing the plunger inwardly along said axis from a gripping position to a released position, said cavity portion having one or more aperture(s) (7) and said plunger having one or more aperture(s) (8) through which one or more suture(s) (9) can extend generally transversely of said axis, wherein said slide-spring lock mechanism is in sliding engagement with one or more length(s) of suture material, said slide-spring lock mechanism being capable of releasable locking engagement along said length(s) of suture material.

In a preferred embodiment, said slide-spring lock mechanism is biased to lock said suture material, and to release said suture material upon application of sufficient force to place said one or more aperture(s) in said cavity portion and said plunger in an essentially coaxial orientation. A preferred biasing device is a coil spring (10).

In another preferred embodiment, said body is integrally formed.

Suture Materials and Suturing Techniques

A suture is a thread that approximates and maintains tissues until the natural healing process has provided a sufficient level of wound strength or compresses blood vessels in order to stop bleeding.

Suture Materials. Sutures can be classified into one of two groups, absorbable and nonabsorbable. Absorbable sutures are, as the name implies, temporary due to their ability to be "absorbed" or decomposed by the natural reaction of the body to foreign substances. An absorbable suture is one that loses its tensile strength within 60 days. Not all absorbable sutures have the same resistance level to absorption, but each can be formulated or treated in order to obtain a desired decomposition rate. Nonabsorbable sutures are, in like manner, sutures that are not dissolved or decomposed by the body's natural action. Such sutures are generally not naturally occurring materials, with the exception of silk; silk and nylon, while being classified as nonabsorbable, actually dissolve after a long period of time compared to that of other absorbable materials.

Sutures are manufactured with a wide variety of parameters. They can be monofilament or many filaments twisted together, spun together, or braided. They can also be dyed, undyed, coated, not coated.

Currently, sutures are designed to result in the most desirable effect for any given situation as determined by those administering the sutures. Taken into consideration in the manufacture and use of sutures are properties such as stress-strain relationship, tensile strength and rate of retention, flexibility, intrinsic viscosity, wettability, surface morphology, degradation, thermal properties, contact angle of knots, and elasticity.

Properties such as stress-strain relationship and tensile strength have a direct effect on how much force at a given rate the closure will be able to withstand. For example, a cough would impose a fast rate of elongation whereas edema or hemorrhage would impose a slow rate of elongation. Surface morphology, the description and condition of the outer surface of the suture, has a direct effect on how the tissue in which the suture is located is affected when the suture is applied. For example, a braided suture can cause a type of sawing effect at the insertion points into the tissue. Flexibility in relation to tensile strength is also of high priority in suture manufacture. Some materials are braided because they become too stiff for handling if formed into monofilaments of sufficient diameter and strength to hold the tissue edges together. Rate of degradation is important due to the difference of required periods of time that a suture is needed to maintain its strength and placement within the tissue. Suture application includes the knotting or tying off of the suture ends. Knotting causes a severe decrease of strength in the suture material, thus when there is a break in the suture, it occurs most frequently at the site of the knot. Selection of the best suture for a given situation involves consideration of all of these factors to produce the most efficient and best suited material.

Some important suture characteristics include tensile strength, as related to suture size and as related to weight required to break a suture; knot strength; force required for a knot to slip; configuration, either monofilament, which has less risk of infection, or braided multifilament, which is easier to handle and tie; elasticity; degree suture stretches and return to original length; memory or suture stiffness, wherein high memory correlates to stiffness, difficult handling, and spontaneous untying; and tissue reactivity, such as the inflammatory response to the suture. In general, preferred suture characteristics include good knot security, inertness, adequate tensile strength, flexibility, ease in handling, nonallergenic nature, resistance to infection, smooth passage through tissue, and, if appropriate, absorbability.

Suture Material Characteristics.

Natural, Absorbable: Plain Catgut is prepared from the submucous coat of sheep or cow intestine. Plain catgut is rapidly hydrolyzed in tissues and loses its integrity within a few days. Generally, it should only be used in tissues where this is not a disadvantage. Catgut has a variable resorption rate, and thus unpredictable tensile strength, and is associated with greater tissue reaction than synthetic materials.

Chromic catgut has been treated with chromic acid salts to affect cross-binding, which delays hydrolysis. Generally, it should not be used where absorption progresses before healing is complete enough to restore adequate tensile strength. Absorption can be unpredictable, particularly in contaminated or infected wounds.

Natural, Non-absorbable: Silk is generally presented as a silicone-coated non-absorbable braid. It has great strength and suppleness, and handles well with secure knots. It is of little use for vascular or dermal locations because it may encourage infection, suture abscesses may leave cosmetically unacceptable scars, and suture sinuses may harbor infection when silk is used in deeper layers. Linen and cotton have similar handling properties, but may be problematic in infected or contaminated wounds.

Metallic sutures are ideal for use in contaminated or dirty wounds. Monofilaments or braids are difficult to manage, as any kinks significantly reduce strength.

Synthetic, Absorbable: Polyglecaprone 25 (Monocryl), polydioxanone (PDS), polyglactin-910 (Vicryl), polyglycolic acid (Dexon), and polycarbonate are braided or monofilament synthetic polymeric sutures which retains their integrity for a significant time in tissue. They handle as well as catgut, and knots are secure, but are degraded by hydrolysis in a slower and more predictable fashion than catgut. These sutures can also be used for buried subcuticular skin closure, thereby avoiding the need for suture removal. There is a risk of minor infection or wound leakage in contaminated surgery.

Synthetic, Non-absorbable: Polyamide nylon, polyester dacron, Polytetrafluoroethylene (PTFE), and polypropylene are not biodegradable, may be more difficult to tie and need several throws for knot security, but glide easily through tissues in monofilament form. Braided synthetics are much easier to handle and are ideal where risk of infection must be minimized.

Suture Sizes. The United States Pharmacopoeia (USP) is the official compendium for the suture industry. It sets standards and guidelines for suture manufacture. Suture sizes are given by a number representing diameter ranging in descending order from 10 to 1 and then 1–0 to 12–0, 10 being the largest and 12–0 being the smallest, at a diameter smaller than a human hair. As sutures were made smaller due to advancement of suture making equipment, USP ran out of ordinal numbers. So, the size smaller than 1 is 0. Smaller than 0 is 00 or 2–0, and so on. For the torso and extremities, 4–0 or 5–0 nonabsorbable sutures, or 3–0 or 4–0 absorbable sutures are generally used. Table I shows the sizes of various sutures:

TABLE I relationship between USP suture size and diameter

| USP Suture sizes | Suture Dia. (mm) |
| --- | --- |
| 2 | 0.500–0.599 |
| 1 | 0.400–0.499 |
| 0 | 0.350–0.399 |
| 2–0 | 0.300–0.349 |
| 3–0 | 0.200–0.299 |
| 4–0 | 0.150–0.199 |
| 5–0 | 0.100–0.149 |
| 6–0 | 0.070–0.099 |
| 7–0 | 0.050–0.069 |
| 8–0 | 0.040–0.049 |
| 9–0 | 0.030–0.039 |
| 10–0 | 0.020–0.029 |

Suturing Techniques. As a method for closing cutaneous wounds, the technique of suturing is thousands of years old. Although suture materials and aspects of the technique have changed, the goals remain the same: closing dead space, supporting and strengthening wounds until healing increases their tensile strength, approximating skin edges for an aesthetically pleasing and functional result, and minimizing the risks of bleeding and infection.

The choice of suture technique depends on the type and anatomic location of the wound, the thickness of the skin, the degree of tension, and the desired cosmetic result. The proper placement of sutures enhances the precise approximation of the wound edges, which helps minimize and redistribute skin tension. Wound eversion is essential to maximize the likelihood of good epidermal approximation. Eversion is desirable to combat the risk of scar depression secondary to tissue contraction during healing. The elimination of dead space, the restoration of natural anatomic contours, and the minimization of suture marks are also important to optimize the cosmetic and functional results.

Many varieties of suture material and needles are available to a surgeon. The choice of sutures and needles is determined by the location of the lesion, the thickness of the skin in that location, and the amount of tension exerted on the wound. Regardless of the specific suture and needle chosen, the basic techniques of needle holding, needle driving, and knot placement remain the same.

The suture needle has 3 sections. The point is the sharpest portion and is used to penetrate the tissue. The body represents the mid portion of the needle. The swage is the thickest portion of the needle and the portion to which the suture material is attached. In cutaneous surgery, 2 main types of needles are used: cutting and reverse cutting. Both needles have a triangular body. A cutting needle has a sharp edge on the inner curve of the needle that is directed toward the wound edge. A reverse cutting needle has a sharp edge on the outer curve of the needle that is directed away from the wound edge, which reduces the risk of the suture pulling through the tissue. For this reason, the reverse cutting needle is used more often than the cutting needle in cutaneous surgery.

The tissue should be stabilized to allow suture insertion. Depending on the surgeon's preference, toothed or untoothed forceps or skin hooks may be used to gently grasp the tissue. Excessive trauma to the tissue being sutured should be avoided to reduce the possibility of tissue strangulation and necrosis. Forceps are necessary for grasping the needle as it exits the tissue after a pass. Prior to removing the needle holder, grasping and stabilizing the needle is important. This maneuver decreases the risk of losing the needle in the dermis or subcutaneous fat, and it is especially important if small needles are used in areas such as the back, where large needle bites are necessary for proper tissue approximation.

Simple Interrupted Sutures. The most commonly used suture in cutaneous surgery is the simple interrupted suture. This suture is placed by inserting the needle perpendicular to the epidermis, traversing the epidermis and the full thickness of the dermis, and exiting perpendicular to the epidermis on the opposite side of the wound. The two sides of the stitch are symmetrically placed in terms of depth and width. In general, the suture has a flask-shaped configuration, that is, the stitch is wider at its base (dermal side) than at its superficial portion (epidermal side). If the stitch encompasses a greater volume of tissue at the base than at its apex, the resulting compression at the base forces the tissue upward and promotes eversion of the wound edges.

Interrupted sutures are comparatively easy to place, have greater tensile strength, and have less potential for causing wound edema and impaired cutaneous circulation. Interrupted sutures also allow the surgeon to make adjustments as needed to properly align wound edges as the wound is sutured. Disadvantages of interrupted sutures include the length of time required for their placement and the greater risk of crosshatched marks across the suture line. The risk of crosshatching can be minimized by removing sutures early to prevent the development of suture tracks.

Simple running sutures. The simple running suture is an uninterrupted series of simple interrupted sutures. The suture is started by placing a simple interrupted stitch, which is tied but not cut. A series of simple sutures are placed in succession without tying or cutting the suture material after each pass. Sutures are evenly spaced, and tension is evenly distributed along the suture line. The line of stitches is completed by tying a knot after the last pass at the end of the suture line. The knot is tied between the tail end of the suture material where it exits the wound and the loop of the last suture placed.

Running sutures are useful for long wounds in which wound tension has been minimized with properly placed deep sutures and in which approximation of the wound edges is good. This type of suture may also be used to secure a split- or full-thickness skin graft. Theoretically, less scarring occurs with running sutures compared with interrupted sutures because fewer knots are made with simple running sutures; however, the number of needle insertions remains the same.

Advantages of the simple running suture include quicker placement and more rapid reapproximation of wound edges, compared with simple interrupted sutures. Disadvantages include possible crosshatching, the risk of dehiscence if the suture material ruptures, difficulty in making fine adjustments along the suture line, and puckering of the suture line when the stitches are placed in thin skin.

Running locked sutures. The simple running suture is locked: the first knot of a running locked suture is tied as in a traditional running suture and may be locked by passing the needle through the loop preceding it as each stitch is placed. This suture is also known as the baseball stitch because of the final appearance of the running locked suture line.

Locked sutures have increased tensile strength; therefore, they are useful in wounds under moderate tension or in those requiring additional hemostasis because of oozing from the skin edges. Running locked sutures have an increased risk of impairing the microcirculation surrounding the wound, and they can cause tissue strangulation if placed too tightly.

Vertical mattress sutures. The vertical mattress suture is a variation of the simple interrupted suture. It consists of a simple interrupted stitch placed wide and deep into the wound edge and a second more superficial interrupted stitch placed closer to the wound edge and in the opposite direction. The width of the stitch is increased in proportion to the amount of tension on the wound. That is, the higher the tension, the wider the stitch.

A vertical mattress suture is especially useful in maximizing wound eversion, reducing dead space, and minimizing tension across the wound. One of the disadvantages of this suture is crosshatching. The risk of crosshatching is greater because of increased tension across the wound and the four entry and exit points of the stitch in the skin. Placing each stitch precisely and taking symmetric bites is especially important with this suture.

The half-buried vertical mattress suture is a modification of the vertical mattress suture and eliminates two of the four entry points, thereby reducing scarring. The half-buried vertical mattress suture is placed in the same manner as the vertical mattress suture, except that the needle penetrates the skin to the level of the deep part of the dermis on one side of the wound, takes a bite in the deep part of the dermis on the opposite side of the wound without exiting the skin, crosses back to the original side of the wound, and exits the skin. Entry and exit points therefore are kept on one side of the wound.

The pulley suture is another modification of the vertical mattress suture. When pulley sutures are used, a vertical mattress suture is placed, the knot is left untied, and the suture is looped through the external loop on the other side of the incision and pulled across. At this point, the knot is tied. This new loop functions as a pulley, directing tension away from the other strands. The pulley suture facilitates greater stretching of the wound edges and is used when additional wound closure strength is desired.

Far-near Near-far Modified Vertical Mattress Sutures. Another stitch that serves the same function as the pulley suture is the far-near near-far modification of the vertical mattress suture. The first loop is placed approximately 4–6 mm from the wound edge on the far side and approximately 2 mm from the wound edge on the near side. The suture crosses the suture line and reenters the skin on the original side at 2 mm from the wound edge on the near side. The loop is completed, and the suture exits the skin on the opposite side 4–6 mm away from the wound edge on the far side. This placement creates a pulley effect.

The pulley suture is useful when tissue expansion is desired, and it may be used intraoperatively for this purpose. The suture is also useful when beginning the closure of a wound that is under significant tension. By placing pulley stitches first, the wound edges can be approximated, thereby facilitating the insertion of buried sutures. When wound closure is complete, the pulley stitches may be either left in place or removed if wound tension has been adequately distributed after insertion of the buried and surface sutures.

Horizontal Mattress Suture. The horizontal mattress suture is placed by entering the skin 5 mm to 1 cm from the wound edge. The suture is passed deep in the dermis to the opposite side of the suture line and exits the skin equidistant from the wound edge. The needle reenters the skin on the same side of the suture line 5 mm to 1 cm lateral of the exit point. The stitch is passed deep to the opposite side of the wound where it exits the skin and the knot is tied.

The horizontal mattress suture is useful for wounds under high tension because it provides strength and wound eversion. This suture may also be used as a stay stitch to temporarily approximate wound edges, allowing insertion of simple interrupted or subcuticular stitches. The temporary stitches are removed after the tension is evenly distributed across the wound. In addition to the risk of suture marks, horizontal sutures have a high risk of tissue strangulation and wound edge necrosis if tied too tightly. Taking generous bites, using bolsters, and cinching the suture only as tightly as necessary to approximate the wound edges may decrease the risk, as does removing the sutures as early as possible. Placing sutures at a greater distance from the wound edge facilitates their removal.

Half-buried Horizontal Sutures. The half-buried horizontal suture or tip stitch begins on the side of the wound on which the flap is to be attached. The suture is passed through the dermis of the wound edge to the dermis of the flap tip. The needle is passed laterally in the same dermal plane of the flap tip, exits the flap tip, and reenters the skin to which the flap is to be attached. The needle is directed perpendicularly and exits the skin; then, the knot is tied.

Buried Horizontal Mattress Suture. The buried horizontal mattress suture is placed in the mid-to-deep part of the dermis to prevent the skin from tearing. If tied too tightly, the suture may strangulate the approximated tissue. The buried horizontal mattress suture is used to eliminate dead space, reduce the size of a defect, or reduce tension across wounds.

Purse-string Suture. In the purse-string suture, a continuous stitch is placed, paralleling the edges of a wound. The wound edges are inverted when tied. The purse-string suture is commonly used to close circular wounds.

Suture removal. In general, sutures should be removed within 1–2 weeks of their placement, depending on the anatomic location. Prompt removal reduces the risk of suture marks, infection, and tissue reaction. However, to prevent dehiscence and spread of the scar, sutures should not be removed too soon. As a general rule, the greater the tension across a wound, the longer the sutures should remain in place. Buried sutures, which are placed with absorbable suture material, are left in place because they dissolve.

Proper suture removal technique is important to maintain good results after sutures are properly selected and executed. Sutures should be gently elevated with forceps, and one side of the suture should be cut. Then, the suture is gently grasped by the knot and gently pulled toward the wound or suture line until the suture material is completely removed. If the suture is pulled away from the suture line, the wound edges may separate. Steri-Strips may be applied with a tissue adhesive to provide continued supplemental wound support after the sutures are removed.

EXAMPLES

The following examples are illustrative of the present invention and are not intended to be limitations thereon.

Example 1

Results of Prototype Testing

The following example illustrates the results obtained during the use of a prototype of a device of the present invention, which has been tested in a cohort of 161 patient examples. Outcomes of all patients at the University of Pennsylvania and the University of Toronto who undergo this method of dialysis shunt puncture site closure continue to be followed, including procedural success rates and duration of placement.

Data was gathered prospectively with followup via review of the dialysis records and clinical examination at time of next intervention for a mean of 4 months (2 weeks to 17 months). Within the 18 month study period, 161 hemostasis devices were placed in 106 patients, of which 40 were female (38%) and 66 were (62%) male. The patients ranged in age from 23 to 83 years (mean, 56.4 years). Hemostasis devices were placed in 106 grafts and 55 fistulae.

Procedures performed included 17 central vein angioplasties/stent placements, 45 declotting procedures, and 98 balloon angioplasties for stenoses. The sheath sizes ranged from 5–10 Fr. The most commonly used sheath sizes were 6 Fr. (56 punctures) and 7 Fr. (36 punctures). In 10 instances, 10 Fr. sheaths were used. In these 10 instances, there were nevertheless no complications related to application of the hemostasis device.

The inventive methods alone were successful in achieving hemostasis in 140 of 161 placements (87%) in the total of 106 patients. In 8 of 161 instances (5%), the suture was broken during application, and manual compression was used to achieve hemostasis. In 11 cases (7%), the patient bled through the suture, and manual pressure was used to aid hemostasis. In 2 applications (1%), hemostasis was not obtained prior to patient discharge, and the purse string suture was tied and the patient discharged, with removal of the suture in 2–4 days time by a dialysis nurse. There were no false aneurysms, hematomata or access thromboses that could be attributed to the use of this technique.

The invention being thus described, it will be obvious that the same may be modified or varied in many ways. Such modifications and variations are not to be regarded as a departure from the spirit and scope of the invention and all such modifications and variations are intended to be included within the scope of the following claims.

We claim:

1. A releasable hemostasis device comprising:
   (i) a body comprising two hollow shaft portions, each having one or more exterior wall(s) and an internal channel, and a cavity portion located between said shaft portions; and
   (ii) a slide-spring lock mechanism within said cavity portion for providing a suture-locking effect within the hemostasis device, said slide-spring lock mechanism having a plunger mounted slidably in a passage for movement relative to said cavity portion along a predetermined axis, and having an end portion which is accessible from the outside of the cavity portion for manually pressing the plunger inwardly along said axis from a gripping position to a released position, said cavity portion having one or more aperture(s) and said plunger having one or more aperture(s) through which one or more suture(s) can extend generally transversely of said axis,
   wherein said slide-spring lock mechanism is in sliding engagement with one or more length(s) of suture material, said slide-spring lock mechanism being capable of releasable locking engagement along said length(s) of suture material.

2. The releasable hemostasis device of claim 1, wherein said slide-spring lock mechanism is biased to lock said suture material, and to release said suture material upon application of sufficient force to place said one or more aperture(s) in said cavity portion and said plunger in an essentially coaxial orientation.

3. The releasable hemostasis device of claim 1, wherein said body is integrally formed.

* * * * *